(12) United States Patent
Madani et al.

(10) Patent No.: US 9,395,362 B2
(45) Date of Patent: Jul. 19, 2016

(54) WESTERN BLOT KIT FOR DETECTION OF VACCINATED POULTRY

(75) Inventors: Rasool Madani, Karaj (IR); Seyed Mahdi Rezayat, Tehran (IR); Saeed Sarkar, Tehran (IR); Tara Emami, Karaj (IR)

(73) Assignee: NANO JAV DARU COMPANY, Tehran (IR)

( * ) Notice: Subject to any disclaimer, the term of this patent is extended or adjusted under 35 U.S.C. 154(b) by 843 days.

(21) Appl. No.: 13/636,713

(22) PCT Filed: Oct. 18, 2010

(86) PCT No.: PCT/EP2010/065626
§ 371 (c)(1),
(2), (4) Date: Sep. 24, 2012

(87) PCT Pub. No.: WO2012/052047
PCT Pub. Date: Apr. 26, 2012

(65) Prior Publication Data
US 2013/0017536 A1      Jan. 17, 2013

(51) Int. Cl.
| | | |
|---|---|---|
| *C12Q 1/70* | (2006.01) |
| *G01N 21/76* | (2006.01) |
| *G01N 33/543* | (2006.01) |
| *G01N 33/553* | (2006.01) |
| *G01N 33/569* | (2006.01) |

(52) U.S. Cl.
CPC ........ *G01N 33/54346* (2013.01); *G01N 33/553* (2013.01); *G01N 33/56983* (2013.01); *G01N 2333/11* (2013.01); *G01N 2469/20* (2013.01)

(58) Field of Classification Search
None
See application file for complete search history.

(56) References Cited

U.S. PATENT DOCUMENTS

2010/0032296 A1    2/2010    Pluskal et al.

FOREIGN PATENT DOCUMENTS

WO    2010017109    2/2010

OTHER PUBLICATIONS

Duchesne et al., Analytical Biochem 2007 vol. 362, pp. 287-289.*
Suarez, Biologicals vol. 33, Issue 4, Dec. 2005, pp. 221-226.*
Duchesne et al., "Silver and gold nanoparticle-coated membranes for femtomole detection of small proteins and peptides by Dot and Western blot," Analytical Biochemistry, vol. 362, issue 2, Mar. 15, 2007, pp. 287-289 (3 pages).
Tumpey et al., "Diagnostic Approach for Differentiating Infected from Vaccinated Poultry on the Basis of Antibodies to NS1, the Nonstructural Protein of Influenza A Virus," J. Clin. Microbiol., vol. 43, No. 2, Feb. 2005, pp. 676-683 (8 pages).

* cited by examiner

*Primary Examiner* — Shanon A Foley
*Assistant Examiner* — Myron Hill

(57) ABSTRACT

Modified western blot membranes with silver nanoparticle allow the small peptides of the NS1 protein of the poultry influenza virus to be kept in the membrane and not to diffuse during transferring from the Tricine SDS PAGE. These peptides may differentiate infected from vaccinated poultry.

3 Claims, No Drawings

SEQUENCE LISTING

```
<160> NUMBER OF SEQ ID NOS: 2

<210> SEQ ID NO 1
<211> LENGTH: 14
<212> TYPE: PRT
<213> ORGANISM: Avian influenza virus

<400> SEQUENCE: 1

Gly Asp Ala Pro Phe Leu Asp Arg Leu Arg Arg Asp Gln Lys
1               5                   10

<210> SEQ ID NO 2
<211> LENGTH: 13
<212> TYPE: PRT
<213> ORGANISM: Avian influenza virus

<400> SEQUENCE: 2

Leu Arg Arg Asp Gln Lys Ala Leu Lys Gly Arg Gly Ser
1               5                   10
```

WESTERN BLOT KIT FOR DETECTION OF VACCINATED POULTRY

CROSS-REFERENCE TO RELATED APPLICATIONS

This application is the National Stage of International Application No. PCT/EP2010/065626, filed Oct. 18, 2010. The content of the above application is incorporated by reference in its entirety.

SPONSORSHIP STATEMENT

This application has been financially sponsored for international filing by the Iranian Nanotechnology Initiative Council.

FIELD OF THE INVENTION

The disclosed kit can differentiate between influenza infected poultry and vaccinated poultry during an influenza outbreak.

BACKGROUND OF THE INVENTION

Differentiating infected from vaccinated animals is known as the DIVA strategy. Vaccination is primarily performed using killed whole virus-adjuvanted vaccines. Proper vaccination may reduce or prevent clinical signs, reduce virus shedding in infected birds, and increase the resistance to infection.

One limitation of killed whole virus-adjuvanted vaccines is that vaccinated birds cannot be distinguished serologically from naturally infected birds using commonly available diagnostic tests. Thus detection of avian influenza becomes much more difficult and often results in trade restrictions because of the inability of the DIVA strategy to distinguish between vaccinated and infected individuals.

The most common method to distinguish vaccinated individuals from infected individuals is the use of unvaccinated sentinels. A second approach is the use of subunit vaccines targeted to the hemagglutinin protein allowing serologic surveillance to the internal proteins. A third strategy is to vaccinate with a homologous hemagglutinin to the circulating field strain, using a heterologous neuraminidase subtype. Serologic detection can then be performed for the homologous neuraminidase subtype as evidence of natural infection. A fourth strategy is to measure the serologic response to the nonstructural protein 1 (NS1). The NS1 protein is produced in large quantities in infected cells, but it is not packaged in the virion. Since killed virus-adjuvanted vaccines for influenza are primarily made with whole virions, a differential antibody response can be seen between naturally infected and vaccinated animals. However, poultry vaccines are not highly purified, and they contain small amounts of the NS1 protein.

Although vaccinated chickens will produce low levels of antibody to the NS1 protein, virus infected chickens will produce higher levels of NS1 antibody, and the two groups can be differentiated. All four DIVA strategies have advantages and disadvantages, and further testing is needed to identify the best strategy to make vaccination a more viable option for avian influenza.

In 2005, Terrence M. Tumpey produced a recombinant NS1 protein in *Escherichia Coli* and developed an ELISA and western blot method to measure the antibody in infected poultry against the NS1 protein. In this research, the reaction band in western blot was shown. Tumpey even introduced two sequences of antigenic peptides in the NS1 protein which have an important role in producing the antibody.

They developed an ELISA system with these peptides to differentiate between the infected and vaccinated poultry, but because of the small size of the peptides, it was not possible to develop a western blot method. ELISA is a colorimetric test and it must be confirmed with other tests like western blot.

In 2007, Laurence Duchesne developed a western blot method for detection of low molecular weight peptides. They made a coated metal like membrane to keep the peptides on the membrane so the peptides will not be washed out through the membrane during washing.

In this invention, the conserved peptide of the NS1 protein is applied to detect the antibody against peptide antigen in infected poultry to differentiate infected poultry from vaccinated ones. This peptide will be transferred from the gel to the silver nanoparticle-coated membrane. This will be done through a western blot process and the peptide antigen will react with the antibody which is present in infected serum. In fact, this methodology may be generalized to any protein having one or more conserved peptide regions and may thus be used in other contexts wherein it is necessary to differentiate between vaccinated, naturally resistant and infected individuals.

DETAILED DESCRIPTION

Avian influenza is a viral disease of poultry which causes a wide range of disease symptoms. During avian influenza outbreak, it is difficult to differentiate infected poultry from vaccinated poultry, because the titer of the antibody in vaccinated poultry is high enough to cross-link with the serum antibody of the infected poultry. It is to be clearly understood that the kit may be used in any context where it is desirable to differentiate between vaccinated and infected individuals of any kind such as e.g. humans, cattle, poultry and pork. Consequently, the kit may be used to discriminate between infected and vaccinated individuals in the context of any infectious disease, such as e.g. avian influenza or diseases caused by coxsackievirus, hepatitis A virus, poliovirus, rhinovirus, herpes simplex type 1, herpes simplex, type 2, varicella-zoster virus, Epstein-Barr virus, human cytomegalovirus, human herpesvirus, hepatitis B virus, hepatitis C virus, yellow fever virus, dengue virus, West Nile virus, HIV, measles virus, mumps virus, parainfluenza virus, respiratory syncytial virus, human metapneumovirus, papillomavirus, rabies virus, Rubella virus, human bocavirus, and parvovirus B19. The kit may thus utilize any conserved part of a peptide or protein of any of the mentioned viruses and the kit may furthermore use one or more of such conserved regions, such as e.g. two or more, 3 or more, 4 or more, and 5 or more conserved regions of a peptide or protein of a virus. In this kit, two conserved peptides of the NS1 protein are chosen to differentiate infected poultry from vaccinated ones. NS1 is a conserved nonstructural protein of the influenza A virus. There is a very low concentration of antibody against this antigen in vaccinated poultry.

Western blot is an accurate method of assaying a protein in the biologic sample. In general methods of western blot, samples are applied to a polyacrylamide gel to separate the protein through an electrophoresis technique. The proteins which have been separated into discrete bands, subsequently are transferred to a membrane (Polyvinylidene Fluoride (PVDF) or nitrocellulose), then the membranes are exposed to the antibody. If the antigen is present in the membrane, the antibody will bind to it and the excess antibodies which are free in the membrane will be washed out. In the next step, the membranes are treated with the secondary antibodies which are labeled with a HRP enzyme. The enzyme will react with a substrate and generate a colored product. In the case where the substrate is luminal, the reaction will be visualized by a Chemidoc apparatus, and the substrate is more sensitive. This technique is a confirmation test. However, it is to be clearly understood that any substrate that is suitable for detection of fluorescence may be used.

In the western blot of the present study, the antigens are peptides but may also be proteins. Two sequences of the peptides as following are synthesized, Peptide A: NH2-GDAPFLDRLRRDQK-COOH (SEQ ID NO 1) (MW: 1686, 9), and Peptide B: NH2-LRRDQKALKGRGS-COOH (SEQ ID NO 2) (MW: 1484, 73). These peptides are loaded in a Tricine-SDS-PAGE (sodium dodecyl sulfate polyacrylamide gel electrophoresis). The low molecular weight of the peptide during transferring from the gel to the membrane may cause its diffusion through the membrane by applying the voltage. Doing western blot with low molecular weight antigens like peptides is difficult. To keep the peptides in the membrane, silver nanoparticle may be used as blocker against diffusion of the peptides. The high affinity binding of noble metals to proteins is attributed to the affinity of the thiols (SH in Cys) and of the amino groups (Arg,Lys,His,amides of Asn,Gln, and the peptide bond) toward these metals. Consequently, not only silver but e.g. copper, platinum and gold may be used according to the invention applicable to any peptide sequence. The peptides were loaded in the Tricine-SDS-PAGE gel; this gel is commonly used to separate proteins in the mass range 1-100 kDa. It is the preferred electrophoretic system for the resolution of proteins smaller than 30 kDa. The concentration of acrylamide used in this gel is lower than in other electrophoretic systems. These lower concentrations facilitate electro blotting, which is particularly crucial for hydrophobic proteins (Nature Protocol, Hermann Schagger, 2006).

The PVDF membranes which are used in this study could be functionalized with silver nanoparticle.

Colloidal silver nanoparticles (around 10 nm) are used to treat the PVDF membrane to avoid peptide diffusion during application of the voltage. The functional group of the amino acids will react with the silver nanoparticles in the membrane. The membrane will be blocked in %5 BSA. Then, the membrane is treated with serum and the peptides bind to the antibodies in the infected serum. The membrane is washed to remove unbounded antibody and then treated with the secondary antibody conjugated with HRP enzyme. The membrane is washed to remove unbound conjugated antibody and then is treated with the luminal substrate. The substrate reacts with the enzyme and a colored product will be produced from a colorless one. The luminal substrate reaction can be visible with a Chemidoc apparatus.

Antibody against NS1 peptide is present in the infected serum and a very low concentration in the serum of the vaccinated poultry. This test could differentiate infected poultry from vaccinated.

EXAMPLES

The detailed components of the detection kit of this example are listed as follows:

Example 1

To develop the western blot kit, four kinds of poultry serum were provided: the first was influenza infected serum collected from infected chickens in the field, the second was vaccinated serum collected from chickens which are given influenza vaccine, the third was experimental infected serum collected from chickens which are infected with H9N2 antigen and the fourth was normal serum collected from healthy chickens.

Example 2

Peptide sequences where synthesized by Metabion Co. (Germany). The antigens (peptides) with 150 ng/µl concentration were diluted in sample buffer and run in the Tricine-SDS-PAGE gel with a size marker. The protein size marker was purchased from sigma, Cat NO: M3546 Ultra low range molecular weight marker (M.W. 1060-26600). 16.6% Urea Tricine-SDS-PAGE made by the protocol which is published by Hermann Schagger in Nature Protocols 1, 16-22 (2006). Electrophoresis was conducted at 40 v at room temperature and after each 30 min, the voltage was increased in 10 v increments till 80 v, and until the dye front was near the bottom of the gel.

Example 3

To prepare the Tricine SDS PAGE gel in example 2, the following procedure must be done:
GEL BUFFER PREPARATION:

|  | Anode buffer (10X) | Cathode buffer (10X) | Gel buffer (3X) |
| --- | --- | --- | --- |
| Tris (M) | 1.0 | 1.0 | 3.0 |
| Tricine (M) | — | 1.0 | — |
| HCL (M) | 0.225 | — | 1.0 |
| SDS (%) | — | 1.0 | 0.3 |
| pH | 8.9 | 8.25 | 8.45 |

16%/6M Urea Mini Gel:

|  |  | 4% stacking gel | 16%/6M Urea (resolving gel) |
| --- | --- | --- | --- |
| AB-3 | ml | 0.5 | — |
| AB-6 | ml | — | 5 |
| Gel buffer (3X) | ml | 1.5 | 5 |
| Glycerol | g | — | — |
| Urea | g | — | 5.4 |
| Add water to final volume |  | 6 | 15 |
| Polymerized by adding: |  |  |  |
| APS (10%) | µl | 45 | 50 |
| TEMED | µl | 5 | 5 |

AB-3:, 49.5% acrylamide., 3% bisacrylamide.
AB-6: 49.5% acrylamide, %6 bisacrylamide,

Example 4

To do blotting, some parts of the gel which contain peptides must be cut thoroughly from the wells where the peptides are loaded. We used PVDF membranes for western blot (sigma: P4188, 0.450. The membranes are cut just for the size of the gels. The gels are incubated in transfer buffer shaking for 2-5 min. PVDF membranes must be prepared as following: 1. PVDF must be washed with 70% ethanol, 2. rinsed with water, 3. incubated for 40 min in silver nanoparticles with agitation, 4. rinsed with water twice, 5. and shook in transfer buffer for 10 min. The transfer buffer consists of: Tris 40 mM, Tricine 40 mM, 0.04% SDS, and 20% Methanol.

Example 5

Silver nanoparticles which are used in example 4 were synthesized as following: the products which are needed are: silver nitrate $AgNO_3$, Trisodium citrate, and $NaBH_4$. Before synthesis, these buffers must be prepared: 1. silver nitrate at 100 mM (10 ml), 2. Trisodium citrate at 50 mM (10 ml), and 3. $NaBH_4$ at 100 mm (10 ml) then 10 mM solution in $H_2O$, all in milliQ $H_2O$. Silver nanoparticles synthesizing must be done as the following procedure: pour 200 ml of $H_2O$ in a flask under stirring, add of 500 µl of $AgNO_3$ 100 mM (0.25 mM final), wait 1 min then add 1 ml of Trisodium citrate 50 mM (0.25 mM final), wait 1-2 min and then add 6 ml of $NaBH_4$ 10 Mm, where the solution gets yellow/brownish very quickly. Around 15 seconds after the addition of $NaBH_4$ 10 mM, remove the solution from the stirrer, leave for around 10 min on the bench and then put the solution back on the stirrer for around 30 min.

Example 6

Transfer the peptides in the gel through the membrane with semidry (Bio-Rad), for 30 min at 12V. Then the membranes are blocked in the PBST with 0.5% BSA for 40 min, after incubation they are washed with PBS 2 times, and then the membranes are incubated overnight in infected serum at 4° C. Then the membranes are washed 3 times with PBST and then the secondary antibody conjugated with HRP is added and incubated for 1.5 hr. The last step is the addition of a luminal substrate, which is purchased from sigma with the Cat No.: CPS 160-1 Kit and the reaction is seen with Chemidoc (Bio-Rad).

SEQUENCE LISTING

Peptide A: NH2-GDAPFLDRLRRDQK-COOH SEQ ID NO 1

Peptide B: NH2-LRRDQKALKGRGS-COOH SEQ ID NO 2

---

---

The invention claimed is:

1. A western blot kit configured to differentiate between influenza-infected poultry and vaccinated poultry, the kit comprising:
    a polyvinylidene fluoride membrane;
    peptide A: NH2-GDAPFLDRLRRDQK-COOH (SEQ ID NO 1) and peptide B: NH2-LRRDQKALKGRGS-COOH (SEQ ID NO 2) of a NS1 protein loaded in a Tricine SDS PAGE gel;
    a chemiluminescence reagent; and
    metal nanoparticles incubated within the polyvinylidene fluoride membrane, wherein the peptide A and the peptide B are transferred to the polyvinylidene fluoride membrane incubated with the metal nanoparticles, and wherein the metal nanoparticles are configured to immobilize peptide A and peptide B of the NS1 protein in the polyvinylidene fluoride membrane by binding to thiols and amino groups of the peptide A and the peptide B, wherein the peptide A and the peptide B are conserved immunogenic peptides of the NS1 protein, react with influenza infected serum antibody, and do not react with vaccinated serum antibody.

2. The kit of claim 1, wherein the metal nanoparticles are homogenous in shape.

3. The kit of claim 1, wherein the metal nanoparticles are nanoparticles of silver, copper, platinum, or gold.

* * * * *